United States Patent [19]

Marini et al.

[11] Patent Number: 4,472,971
[45] Date of Patent: Sep. 25, 1984

[54] ACOUSTIC EMISSION LOCATOR OF DEFECTS IN A CLOSED STRUCTURE

[75] Inventors: Jean Marini, Marly le Roi; Bernard Audenard, Orgeval, both of France

[73] Assignee: Framatome, Courbevoie, France

[21] Appl. No.: 313,922

[22] Filed: Oct. 22, 1981

[30] Foreign Application Priority Data

Nov. 7, 1980 [FR] France .................. 80 23800

[51] Int. Cl.$^3$ .......................................... G01N 29/04
[52] U.S. Cl. ..................................................... 73/587
[58] Field of Search .............................. 73/587, 801

[56] References Cited

U.S. PATENT DOCUMENTS

| | | | |
|---|---|---|---|
| 3,052,115 | 9/1962 | Renaut et al. | 73/622 |
| 3,985,024 | 10/1976 | Horak | 73/587 |
| 4,009,463 | 2/1977 | Vercellotti | 73/587 |
| 4,033,179 | 7/1977 | Romrell | 73/587 |

*Primary Examiner*—James J. Gill
*Attorney, Agent, or Firm*—Pollock, Vande Sande & Priddy

[57] ABSTRACT

The present invention allows the position of a defect to be located when it emits acoustic waves into a closed structure. The waves travel around closed routes in a section of the structure.

To this end, it comprises at least three acoustic sensors (22–24), uniformly distributed on the surface of the section of the structure monitored, connected to logic (26, 27) for encoding the order of arrival of the signals detected. Control means (16, 20, 35) for controlling display means and means (19) for controlling the writing means of the latter, which is preferably a conventional dual-trace oscilloscope are described. The image of the section monitored is traced by two beams rotating in opposite directions, only one of which is illuminated for a brief instant at the moment of detection of the acoustic emission, as it passes the image point identifying the defect.

25 Claims, 10 Drawing Figures

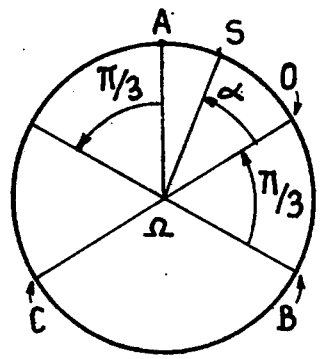
FIG_1-a
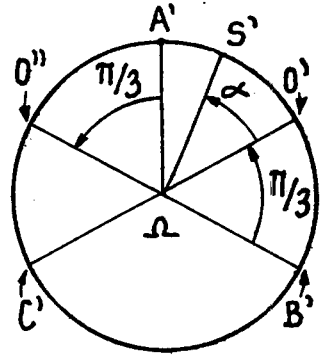
FIG_1-b
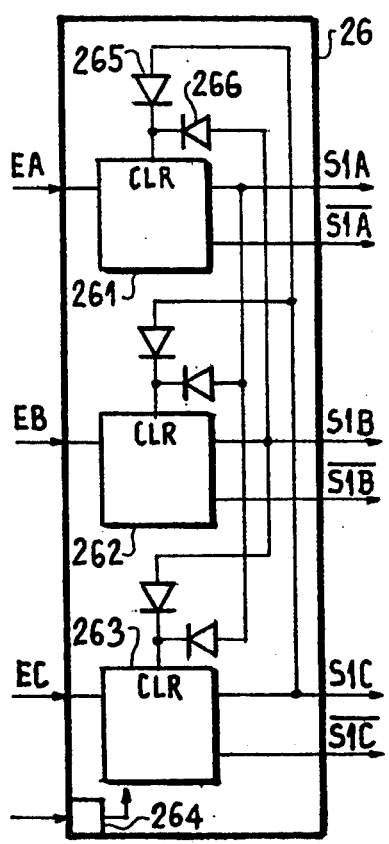
FIG_3
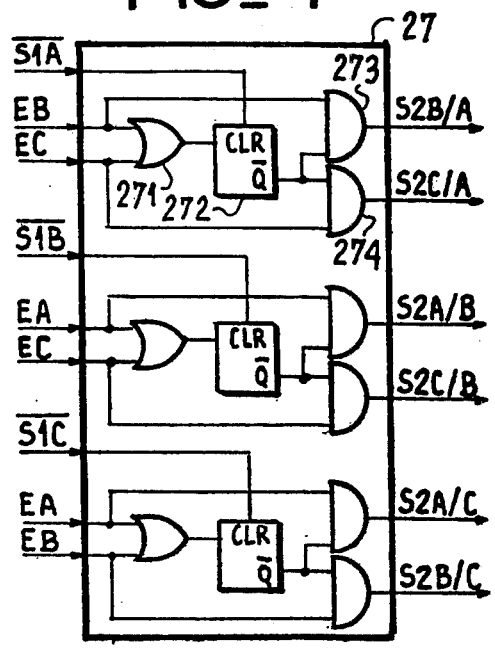
FIG_4
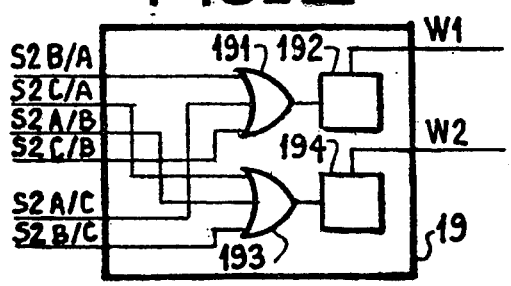
FIG_5

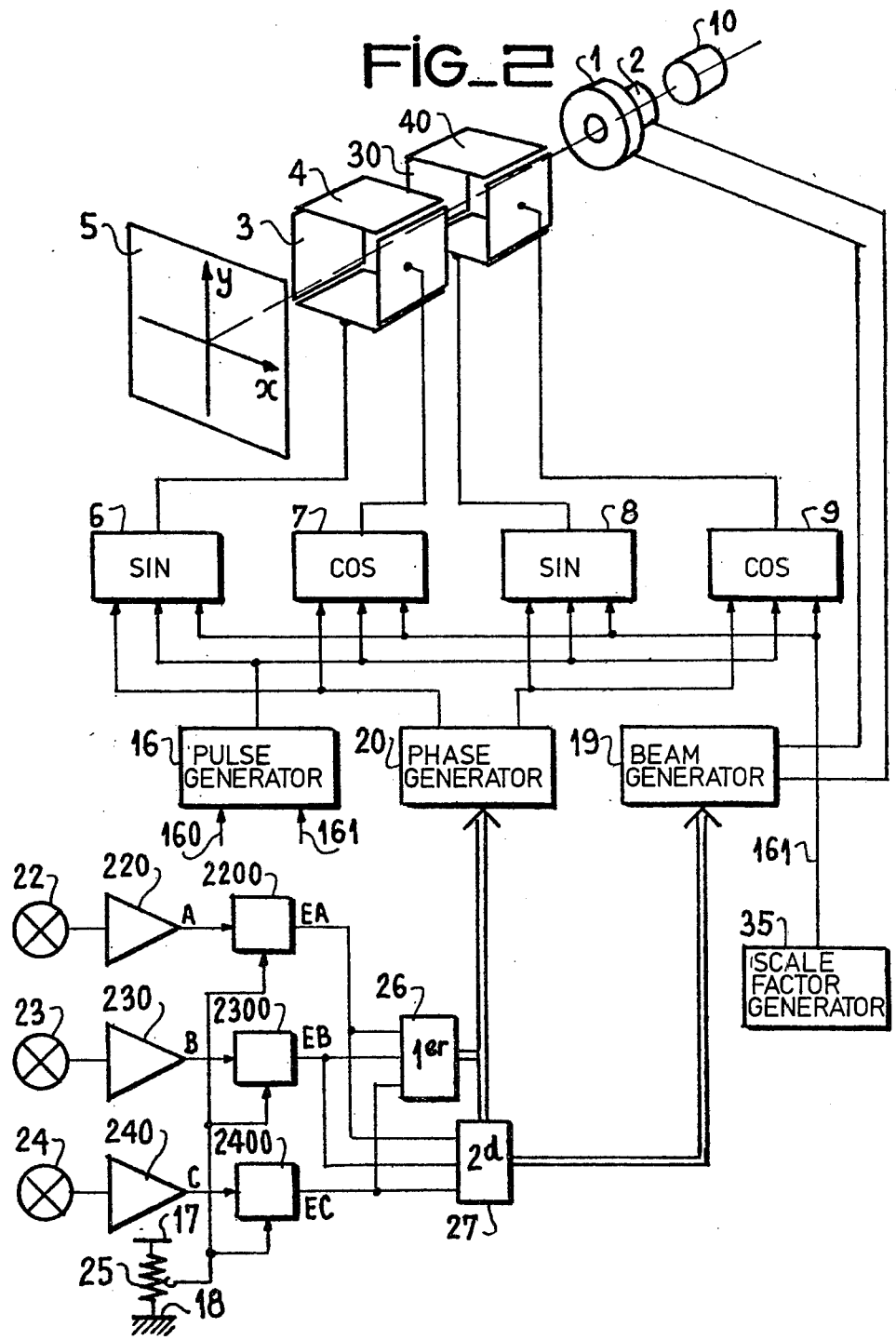

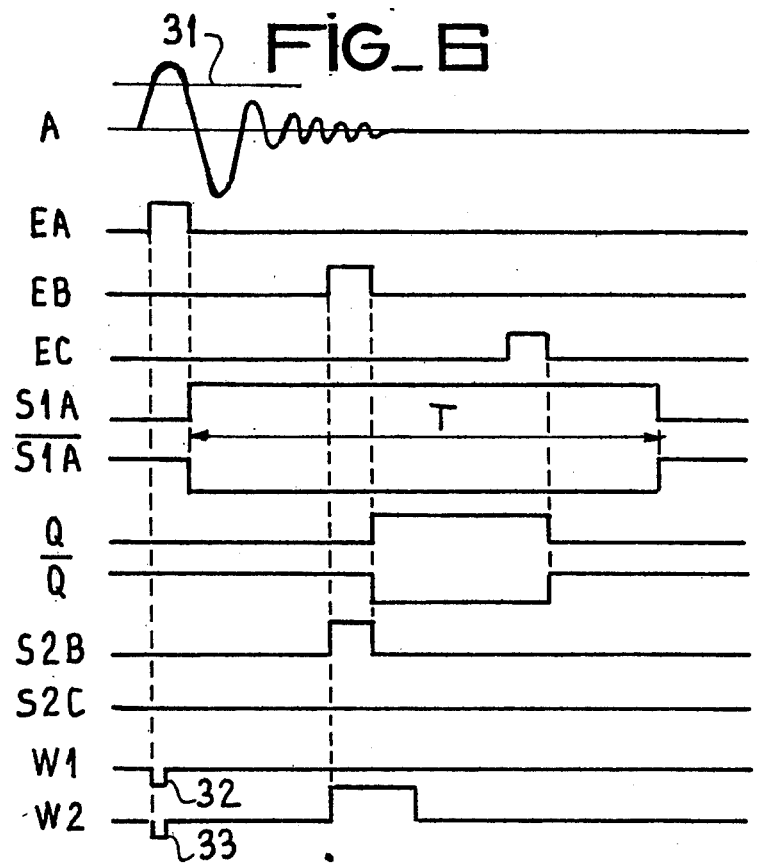
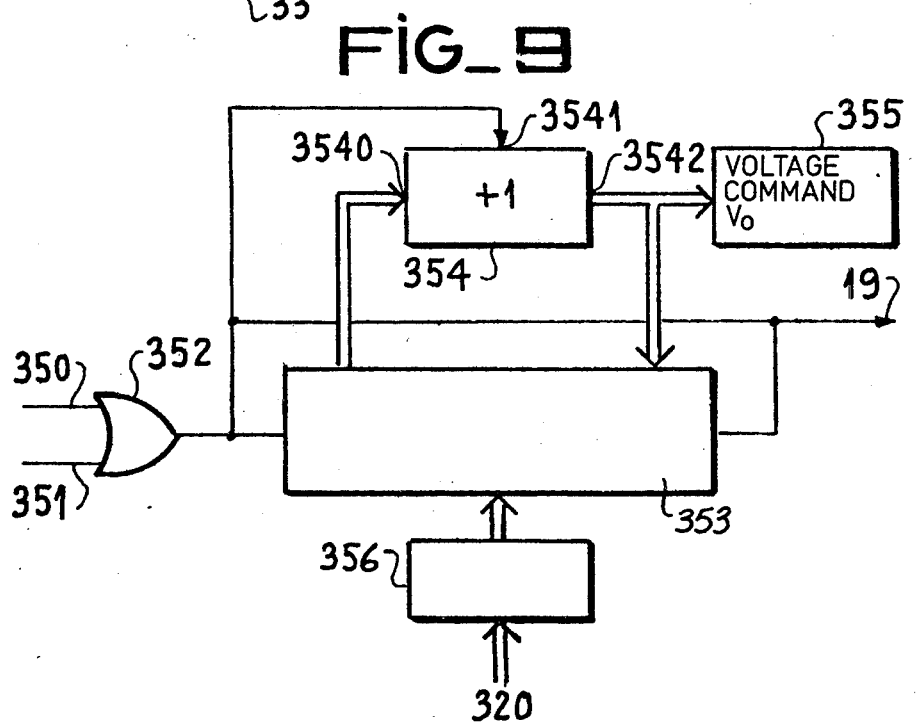

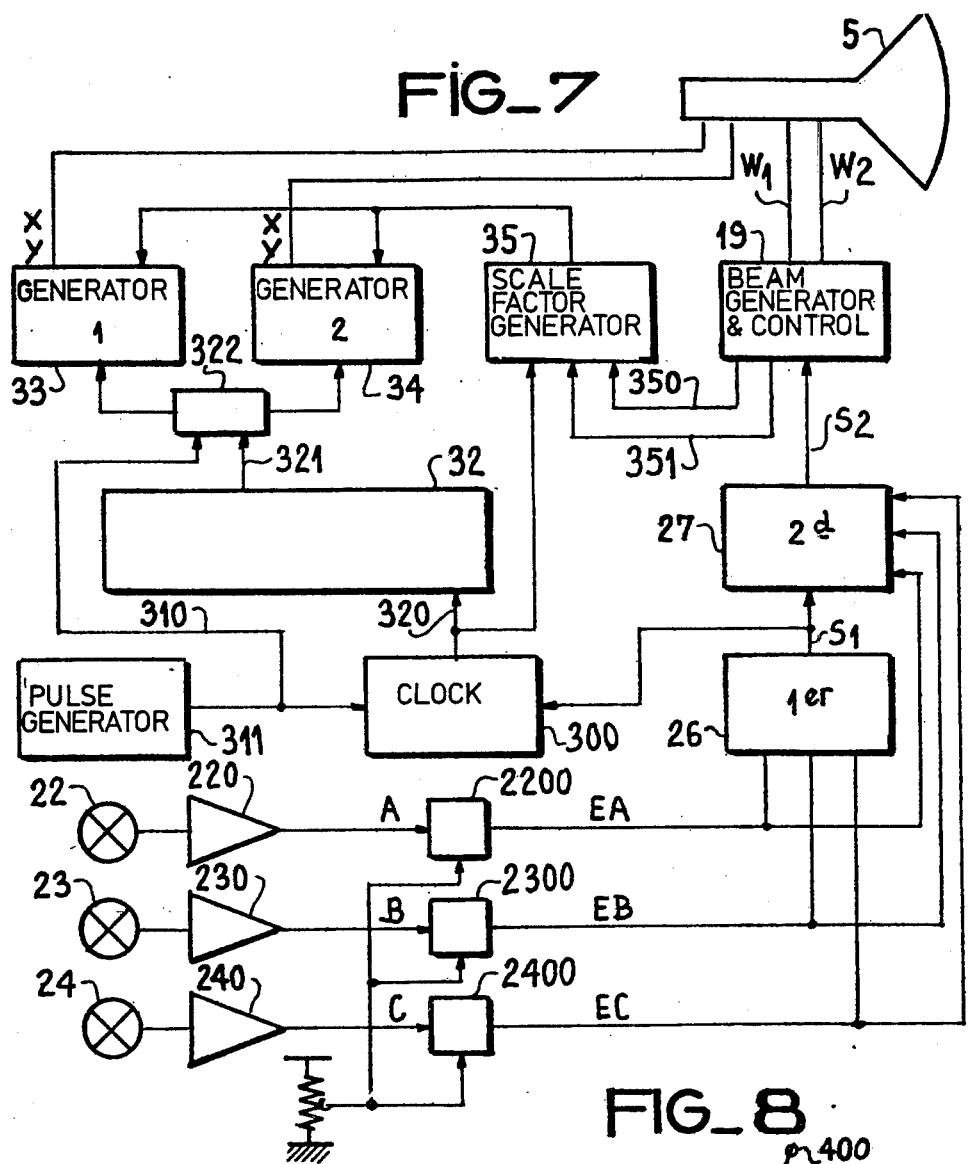
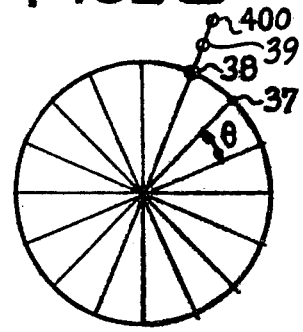

ACOUSTIC EMISSION LOCATOR OF DEFECTS IN A CLOSED STRUCTURE

FIELD OF THE INVENTION

The present invention, arising from the work of M. AUDENARD (CGR Company) and M. MARINI (FRAMATOME Company) concerns a locator of faults by acoustic emission into a closed circuit. It is particularly suited to industrial testing of weld beads on tubes.

PRIOR ART

There are many ductings, pipes, tubes, etc. in an industrial plant. These elements usually serve as conveyors of fluids, heat exchangers etc. They are usually subjected to great temperature or pressure stress, large exchanges of heat, expansion of thermal origin, knocking from the opening of valves, etc.

Casing forming in particular can produce microdefects which are imperceptible under electronic microscope. These defects may also increase in service in an aggressive environment. This increase causes an acoustic emission. It therefore provides a danger warning. An aim of the present invention is to allow efficient monitoring of these submicroscopic defects in a way which can be used in industry.

In addition, ductings, which can be very long, are often constituted by assemblies of tubes laid end to end. A "V"-shaped weld bead is made, for example, at each joint. During welding, defects can be created: inclusion of slag, gas cavities, lack of penetration, etc. These defects are, however, inspected at delivery by X-radiography, gamma-radiography, ultrasonic testing etc.

Acoustic emission monitoring techniques, so-called, have been proposed in the prior art. In practice, under various influences, the defects which appear are of the fissure or fault type. They emit acoustic waves as they grow. As they are very small, they are treated as acoustic point sources. The waves are propagated in various modes, in various directions. Once they have been received by acoustic sensors, they produce signals which are analysed by calculator, the latter being able to supply a certain number of more or less accurate data, ranging from a simple warning when a threshold of given risk is exceeded to complete display of the phenomena.

One of the major disadvantages of these computer-based systems is the excessive cost they constitute when used for constant monitoring of a large assembly. A further advantage of the invention is that it offers a solution to testing by acoustic emission without the help of a computer.

SUMMARY OF THE INVENTION

In practice, according to the present invention, an acoustic emission locator of defects in a closed-circuit structure, represented on display means by writing means, also includes acoustic sensors, and logic for encoding the order of arrival of acoustic signals which actuate the control means of the display means and the control means of the writing means.

BRIEF DESCRIPTION OF THE DRAWINGS

The invention will be more clearly understood and various advantages shown by means of the description and the attached figures which are:

FIGS. 1a and 1b: the views of a circular section of tube and its image on the display means;

FIG. 2: a simplified diagram of an embodiment of the locator according to the invention;

FIGS. 3 to 5: details of FIG. 2 elaborated;

FIG. 6: a diagram of an example of operation;

FIG. 7: a diagram of another embodiment of the locator according to the invention;

FIG. 8: a drawing of the image obtained by the locator described in FIG. 7;

FIG. 9: a detail of FIG. 7.

DETAILED DESCRIPTION OF AN EMBODIMENT

The preferred embodiment, now described, comprises three sensors A, B and C regularly positioned on the periphery of the section of the tube examined. Each sensor A, B or C can be of the piezoelectric or magnetostrictive type or an electric sensor. It transforms an acoustic pulse, received on the surface to which it is coupled, into an electrical signal which is in a certain frequency band which can sometimes extend from 0 to 1 Mhz.

In FIG. 1a, the section 1 of the tube examined is circular. Any other closed shape is also suitable. $\Omega$ designates the centre of symmetry of the section, represented here by a line without thickness. The three sensors A, B and C are positioned 120° apart. The axis $\Omega O$ is arbitrarily chosen as polar reference axis. The radius of the circular section is R. If a defect appears at the point S, this becomes an acoustic source. The mode of propagation of the acoustic wave is in most cases a surface wave if the material of the tube is not very thick and a compression wave if the reverse is true. Each of these modes has a corresponding speed C of propagation of the wave in the section, as a function of the shape of the section, the nature of the material and the various stresses. This speed C can be measured and calibrated with the arrangement according to the invention as described hereinafter.

The acoustic source S has been represented to the right of the sensor A so that the radius vectors $\Omega S$ and $\Omega O$ form an angle $\alpha$. In this configuration the sensor A is the first to receive the acoustic wave from S and the sensor B is then the second to receive the wave. The difference in arrival time is:

$$t = \frac{BS - AS}{C}$$

in which AS and BS are arcs of section which are easily expressed as a function of the angle which subtends them:

$$AS = (\pi/3 - \alpha)R$$

in which $\alpha$ is the angle between the vectors $\Omega S$ and $\Omega O$ and in which R is the radius of the section. With a section which is non-circular but analytically representable, the length (AS) is then a curvilinear integral.

Lastly: $BS = \left(\frac{\pi}{3} + \alpha\right) R$

From which: $t = \frac{2R}{C} \alpha$

There are known sinusoidal generators, with adjustable frequency, controllable initial phase and adjustable output voltage level. With two sinusoidal generators at the same frequency, out of phase by $\pi/2$ with respect to one another and each connected to one or other of the pairs of plates 3, 4, a circle is thus conventionally obtained. The radius of the circle is fixed by the maximum voltage $V_o$ applied to the plates. There will therefore be applied as a function of time:

$$V_{x1} = V_o \cos \omega t$$

to the pair of plates 3 and:

$$V_{y1} = V_o \sin \omega t$$

to the pair of plates 4, $V_o$ representing the radius r of the circle traced on the screen 5.

In normal operation, the oscilloscope used in the invention is only activated when an acoustic pulse is received by a first sensor A, B or C. The detection of the property "first received" triggers the positioning of two beams at $\pi/3$ either side of the images A', B' or C' of the positions of the sensors A, B or C. In the example described in FIGS. 1a and 1b, the point A' on the oscilloscope corresponds to the point A of the section. The beams are positioned at O' and O'' either side of A, the first sensor reached.

In practice, the detection of A, the first sensor reached, clearly indicates that the acoustic source S, a fissure, for example, is located in the third of the section, symmetrically distributed either side of A.

The triggering of the oscilloscope therefore comprises two successive operations very close together: positioning of the two beams either side of the image of the first sensor reached, enabling of the outputs of the various sinusoidal generators.

A notable characteristic of the invention is that the beams scan the section, passing first through the image of the sensor first reached. They then rotate in opposite directions to each other.

FIG. 2 shows two pairs of plates 30, 40 relating to the second electron beam. These two pairs cannot exist physically but exist in time by switching of the plates 3, 4 on the two distinct beams. The sinusoidal generator 6 whose output voltage as a function of the time t is:

$$V_{x1} = V_o \sin(\omega t + P_{x1})$$

is associated with the pair of plates 4, for vertical deflection. In the same way, a similar generator 8 is connected to the pair of plates 40 which receives:

$$V_{x2} = V_o \sin(\omega t + P_{x2})$$

For the horizontal deflection plates 3 and 30 there is:

$$V_{y1} = V_o \cos(\omega t + P_{y1})$$

supplied by the generator $$V_{y2} = -V \cos(\omega t + P_{y2})$$

supplied by the generator.

The factor $\omega$ is the pulse rate or the rate of rotation of the point of impingement of the beam on the screen 5.

The beams are also shown to rotate in opposite directions to each other. This detail of the invention allows the acoustic point source S to be far more rapidly scanned.

Let r be the radius of the circle described by each of the beams, as a function of the value $V_o$. FIG. 1b shows that the beam leaving O', after an angular displacement $\alpha$, reaches the point S' which is the image of the acoustic point source S. This point S' is therefore reached by the first beam at the end of a time $\Delta T$ after its departure. The beam will have travelled a distance $O'S' = v\Delta T = r\alpha$ from the point O' to the point S', moving at a speed v.

$$v = \frac{r\alpha}{R \cdot 2\alpha} \cdot C = \frac{r}{R} \frac{C}{2}$$ can be deduced from the value of $\Delta T$ previously calculated.

With a reduction factor close to r/R, due to going to a reduced image, the linear speed of the spot is therefore smaller than half that of the beam. The speed C can be easily measured by calibrating the locator according to the invention.

The sensors 22-24 are connected to means for shaping the received signal. They are each connected to amplifying channels 220-240 which respectively deliver the signals A, B and C represented in FIG. 6 by a single signal A. Each of the signals A, B or C is injected into a comparator 2200-2400, which receives a d.c. voltage such as 31 in FIG. 6. This voltage, supplied for example by a potentiometer 25 supplied between a maximum voltage 17 and the ground 18 of the apparatus according to the invention, allows logic signals EA, EB or EC to be obtained as outputs resulting from A, B or C as represented by A only in FIG. 6.

The three signals EA, EB and EC are applied to logic 26, 27 for encoding the order of arrival which on the one hand allows which of the sensors A, B or C is first reached by the acoustic wave to be determined by means of a detector 26 of the first sensor reached and on the other the second sensor reached to be determined by means of a detector 27 of the second sensor reached, the first reached being known.

At this stage in the acoustic defect locator according to the invention, the position of any acoustic source is known in the regions, bounded by the sensors and either side of each of them, of angular length $\pi/3$ on the circular section. Only one of the output signals S1A, S1B, S1C of the detector 26 is at the active level, during an acoustic emission, to indicate which of the sensors A, B or C has been reached first. Similarly, only one of the output signals of the detector 27 is at the active level.

In addition, again in FIG. 2, a screen 5 on which a system of orthogonal axes x, y, has been drawn, a first deflection system 3, 4 and a second deflection system 30, 40, as well as a beam generator 1 and a beam generator 2 have been represented in an exploded diagrammatic view of an oscilloscope with two beams. The assembly 10 allows the fine electron beam emitted along the axis represented without reference in FIG. 2 to be created physically.

Two generators 6 and 8, connected to the pairs of horizontal plates 4 and 40, deliver a voltage proportional to $\cos \omega t$, while the generators 7 and 9 connected to the pairs of vertical plates 3 and 30 deliver a voltage proportional to $\sin \omega t$, as seen hereinbefore.

In addition to its biases (not represented), each generator 6-9 of a.c. voltage receives three d.c. control voltages which are the phase control, the pulse rate control and the output level control. The latter control can also be constituted directly by the adjustable gain amplifier positioned at each deflection terminal of a standard oscilloscope.

In the embodiment described, in which the section monitored is a circle, the four output levels are equal and allow the radius r of the image of the section monitored on the screen 5 to be determined.

In addition, with non-circular images, programmed output level controls can be added so as to represent, with two beams travelling in opposite directions, whatever the closed curve, an image of any known section of the structure. The speed of travel of the beams is then proportional to the speed of propagation of the waves in the structure.

Here, there are common generator pulse rate controls. They allow the linear speed v of travel on the screen of the beams issuing from the beam generators 1 and 2 to be fixed as a function of the radius r of the image, the radius R of the section and the speed C of the acoustic waves in the medium. The pulse rate control voltages, identical here to obtain circles, are supplied by a pulse rate generator 16.

The pulse rate generator 16, which in other embodiments can be integrated with the curve generators 6–9, includes a control oscillator of adjustable frequency, a circuit for matching to the curve generators 6–9 and an apparatus for automatic calibration of the frequency. This calibration apparatus, not represented in the drawing, allows an acoustic receiving channel to be used to receive acoustic test waves emitted by any of the sensors. To do this, the sensors must be of the reversible type such as piezoelectric sensors, for example. At least one of them must be connected to a two-position switch. The first position connects the sensor to the calibration apparatus and the second position to the conventional receiving channel already described, corresponding to normal use of the locator.

The calibration apparatus also includes a test pulse generator. Once this is connected to the test sensor-emitter, it emits a series of electrical pulses, which the sensor-emitter transforms into an acoustic wave with bias and characteristics predetermined as a function of the structure and type of defect monitored.

A ramp voltage generator is synchronized with the test pulse generator. This ramp voltage generator includes a circuit for blocking the output level activated by reception of an acoustic wave at the sensor connected in a position to monitor the test for calibration of the propagation speeds. The output voltage of the generator is then supplied to a pulse rate control input of the sinusoidal generators 6–9.

It is proportional
on the one hand to the time of travel of an acoustic wave between two sensors;
on the other hand, as their distance is known, to the speed of propagation of the acoustic wave in the structure monitored.

Phase control of a generator 6–9 allows a term P to be added to the instantaneous phase. This allows a beam to be positioned on any point of the image circle fixed by the pulse rate ω and the radius r. Each term P must be supplied to a pair of generators 6, 8 or 7, 9. Let P and P' be the two phase values. The various output voltages, in the example described, will then be:

$$V_{x1} = V_o \cos(\omega t + P)$$
$$V_{y1} = V_o \sin(\omega t + P)$$
beam from beam generator 1

$$V_{x2} = V_o \cos(\omega t + P')$$
$$V_{y2} = -V_o \sin(\omega t + P')$$
beam from beam generator 2

The values of P or P' are predetermined. In practice, the two beams are required to be positioned at an angle $\pi/3$ either side of the image point of the first sensor reached. It follows from this observation that the various phase controls of the generators 6–9 are supplied by the signals S1A, S1B and S1C which select two values P or P' taken in pairs which are

| first reached | P | P' |
|---|---|---|
| A | 0 | $\frac{2\pi}{3}$ |
| C | $\frac{2\pi}{3}$ | $\frac{4\pi}{3}$ |
| B | $\frac{4\pi}{3}$ | 0 | with the following assumptions:
the beam from the beam generator 1 is, at the initial instant, displaced in phase by P, then rotates in the trigonometrical direction;
the beam from the beam generator 2 is, at the initial instant, displaced in phase by P', then rotates in the antitrigonometrical direction;
the angles are measured from the radius $\Omega'O'$ of FIG. 1b;
the points A', B', C' are in the order depicted in this FIG. 1b.

The initialization is carried out instantaneously at the time the nearby elements respond. This initialization simultaneously triggers the rotation of the beams and immediately the a.c. voltage appears at the output of the generators. All these operations are carried out by the phase generator 20.

By rapid switching such a generator must select two d.c. voltages from among three known ones, each representing a particular phase in the positioning of the beams, on decoding the three inputs S1. While none of the S1 is active, no voltage is supplied by the phase generator 20. The deflections (3, 4; 30, 40) are then inoperative and neither of the two beams is positioned or tracing.

The phase generator 20 physically comprises a switch whose contact is positioned so as to connect two of the voltages supplied by the preselections. These can include voltage sources. In a preferred embodiment, each source can be constituted by an amplifier whose d.c. output level is calibrated. Each of the amplifiers receives one of the signals S1. It is also connected to a voltage divider arrangement which delivers the two voltages corresponding to the predetermined initial phases already described. The amplifiers can include simple transistors arranged to switch a d.c. supply which, at a command to their base connected to one of the signals S1, is connected to one of the voltage divider arrangements described hereinbefore.

The number of sensors can be increased when the section monitored is a closed curve with a change in concavity.

It is also noted that the control for striking the beams is separate from that described hereinbefore. In practice, when a beam physically composed of electrons crosses the space within the plates 3, 4 or 30, 40, the electric field created by the generators 6-9 deflects it toward a particular point on the screen 5 at a given instant. The impact of the flux of electrons on the material constituting the screen 5 creates an emission of light.

When the beam does not comprise electrons, i.e. not enough electrons for the point of impact to be illuminated, the voltages applied to the plates 3, 4, 30, 40 create such conditions that this virtual beam travels around a circle not actually traced on the screen 5. This is illuminated only at the control of the beam generator 1 or 2 from the moment the latter receives the control.

This beam control is produced by a beam control generator 19 which receives the output signals of the detector 27, S2 as input. It selects the beam for illumination and gives the command for illumination when the second sensor is actuated. Illumination lasts T seconds, this time being very small in view of the travel period for the image of the section. This generator can also include a time-delay which gives the command for illumination again at each period following the detection of the acoustic source S. The value of the illumination time T determines the size of the trace of the image point S' of the acoustic source S. The screen 5 can also be of the memory type which retains the trace of the impact.

FIG. 5 shows a simplified beam control generator 19. The output signals S2 of the detector 27 of the second sensor reached by the acoustic wave are decoupled in pairs. There are thus two output signals S2 indicating whether B is the second sensor reached according to whether A or C was the first sensor reached. This allows the use of the signals S1 to be avoided, for the sake of simplicity. The control generator 19 includes two OR logic gates 191 and 193 whose outputs control two pulse generators 192 and 194 whose outputs W1 or W2 drive one or other of the beams concerned.

FIG. 3 shows a particular embodiment of the detector 26 of the first sensor reached. This detector 26 receives the logic signals EA, EB and EC as input. Each of them is applied to control a monostable (respectively 261, 262 and 263) which lengthens the first signal received so that the output level only falls to the passive level after the last signal EA, EB or EC has been received. This time-delay will advantageously have the value of one activation period as duration, i.e. the time also that one of the beams takes to travel around the whole image of the section. The time-delay is implemented by a unit 264 which receives a signal, for example, from the circuit for calculating the pulse rate of the preceding generators 6-9.

Each normal output Q of the monostables thus delivers a signal, respectively to the CLR input (such as 28 of the monostable 261), termed the input for resetting to passive level, of each of the other two monostables. Thus S1A, from the monostable 261, is applied to the CLR inputs of the other two monostables 262 and 263. This has the effect of holding the outputs Q of 262 and 263 at the passive level whatever happens at the inputs EB and EC if EA is at the high level. Thus only one of the signals S1 is able to be at the active level and it designates the first sensor reached properly.

The diodes, such as 265 and 266, are intended to be non-return devices to avoid triggering of the CLR inputs at the wrong moment. In addition, the signals $\overline{S1}$ termed the complementary signals of S1, which are $\overline{S1A}$, $\overline{S1B}$ and $\overline{S1C}$, are also disposed at the output of 26.

FIG. 4 represents a detector 27 of the second sensor reached by the acoustic wave. This detector comprises three multivibrators whose output state at the output terminal Q changes at every trailing edge transition at its input. The detector 27 includes three identical arrangements. Each arrangement has two inputs such as EB and EC which are combined in an OR logic 271. The output state is an active state as soon as there is at least one active state at the input. The output of the "OR" gate 271 is applied to the input of the multivibrator 272.

The multivibrator 272 receives at its resetting the signal $\overline{S1A}$ which is active as long as the sensor A does not detect a signal. As soon as A senses an acoustic signal, $\overline{SLA}$ changes to the inactive level, the resetting CLR input is neutral, the multivibrator 272 is then enabled and operates normally.

Its complementary output $\overline{Q}$ which is in the inactive state between two active states applied at the input is then used. This output $\overline{Q}$ is connected to two AND logics 273, 274 which are composed with EB and EC to give S2B/A and S2C/A, two output signals, whose states are exclusive, i.e. which are also the logic complement of each other.

Thus six signals S2 are obtained, which are: S2B/A, S2C/A, S2A/B, S2C/B, S2A/C, S2B/C, S2 designating a "second sensor reached" detection signal, the first letter following designating the sensor concerned and the second letter separated by a stroke the first sensor reached. Only one of these signals at a time can be at the active level.

The complement $\overline{S1}$ of the output signal corresponding to the first sensor reached is also applied to each multivibrator of the detector at its CLR input, already described. This arrangement allows the multivibrators to be enabled only one by one, i.e. exclusively that concerned with the corresponding signal S1. An example of operation will allow this detail of the invention to be better understood.

The locator described in FIG. 2 also includes a scale factor generator 35. The latter allows development of the signal 161 intended for the pulse rate generator 16 and the output level $V_o$ of the generators 6-9. It includes a potentiometer for adjusting the radius R of the section of the tube and radius r of the circle on the screen. In practice, more simply, a gain control is involved, manually adjustable, and used on each generator 6-9.

An example of the operation of the locator will now be described. The acoustic source S is assumed to be physically positioned as in FIG. 1a. In FIG. 6, the various timing waveforms which indicate the response of the locator in real time are read from bottom to top. The sensors A, B or C receive a signal termed acoustic emission signal. Only the signal A from the sensor A has been represented. The signal can be variously processed. In particular, in the example described here, the signal A is compared with a reference level 31. The comparison of these two signals, effected by the means described hereinafter, provides a signal EA of the digital type. It may require shaping, for example, with a time-delay monostable which is triggered on the rising front of the acoustic wave A and falls again at the end of a duration determined by the time constant of the monostable.

In the case of FIG. 1a, the sensors receive the acoustic wave in the order A, B, and then C. The logic signals EA, EB, EC are shown. The present invention also allows masking of the acoustic waves which activate the sensors after each of them is first activated. In practice, a given sensor receives a first pulse arriving by the most direct route which exists between the emission source and itself, and then a certain number of others arising from secondary emissions or longer paths. Discrimination is achieved here by comparison of the signal received with a sufficiently high given level for all the signals received after the first activation to leave the locator untriggered.

The detector 26 of the first sensor reached is first acted on by EA. The monostable 261 is therefore the first to switch over to the active level. Its output terminal delivers the signal S1A which only falls back to the passive level at the end of a time such that all pulses to be masked have occurred with S1A is at the active level. In practice, this signal, as shown in FIG. 3, is applied to the CLR inputs of the other two monostables 262 and 263 of the detector 26, forcing their two signal inputs to be inoperative. It is thus noted that while S1A is at the active level at which it is kept by the delay time T of the monostable, any new signal EA is also inoperative.

At this stage, the locator according to the invention knows the first sensor reached. The signal S1A is then applied to the phase generator 20 which has the effect of positioning the two beams and projecting the tracing of the circles for the said beams. The working situation at this moment is that the pulse rate generator 16 has received speed data on the wave in the section.

At the same time, in FIG. 6, it is noted that the complementary signals $\overline{S1}$ of the signals S1 block the multivibrators of the detector 27 except for the first 272. This receives the two signals EB and EC successively at its input via the OR gate 271. The multivibrator 272 supplies a signal Q and its complement $\overline{Q}$ which rises to the active level again after the appearance of EC. This has the effect of masking EC at the AND gate 274 and consequently of enabling the AND gate 273 which supplies a signal S2B/A, close to the rise times of the gates, identical to the signal EB.

The signal S2B/A is then supplied to the beam control generator 19 whose OR gate 191, the only one to receive an active level at S2B/A, triggers a pulse generator 192 which supplies a pulse W1, this lighting up the beam rotating in the trigonometrical direction on passing to the image point S' of S on the oscilloscope. When the screen 5 is equipped, for example, with an image memory apparatus, an observer can locate the position of an acoustic source occurring unexpectedly.

Other embodiments according to the invention can be proposed. In particular, triggering of the curve generators 6-9 can be obtained directly by the signals EA, EB, EC, the first to arrive inhibiting the generators 6-9 for those that follow.

Another possible variant uses digital circuits for the whole control. FIG. 7 represents a diagram of such a variant for this. As previously, it comprises three sensors 22-24, the detectors 26, 27 of the logic for encoding the order of arrival, the beam control generator 19 and the dual beam oscilloscope 36. It also includes a pulse rate generator 311, a clock 300, X and Y curve generators 33, 34, and a scale factor generator 35. Lastly a programmed memory 32 of the ROM type, for example, constitutes a curve generator control. In the case of a circular section, the ROM memory 32 is loaded with a sine table.

When testing parts without faults or fissures, the sensors 22-24 receive no activation due to significant acoustic emissions. The screen 5 of the oscilloscope 36 stays blank. The pulse generator 311, suitably initialized as seen hereinbefore, controls a clock 300; in practice, this clock is a generator of addresses and read commands for the ROM memory 32. In other words, the clock 300, at the instant t, controlled by the pulse $\omega$ generator 311, supplies the instantaneous phases or angular positions $\omega t$ for a trigonometrical scan of the image circle for the section of the tested tube. Thus, read commands are sent, with the addresses which correspond to the angular positions of the beam issued from the beam generator W1, over the input line 320 of the ROM 32.

To generate a path in the anti-trigonometrical direction for guiding the beam issued from the beam generator W2, the address n, n being supplied by the clock 300, and the address $N-n$, N being the capacity of the table in ROM 32, are simply read, for example. N is in fact fixed by the resolution of the image required on the screen 5. In practice with $N=360$, 360 angular positions can be scanned for one circle, thereby achieving a resolution of $\theta = 1°$ of arc over the image of the section.

The output line 321 of the ROM 32 is used, therefore, to apply the value $\sin \omega t = \sin (N-n)\theta$ for the path in the anti-trigonometrical direction over a period of time which is $(2\pi)/(N\omega)$, each of the values $\sin n\theta$ and $\sin (N-n)\theta$ being supplied over the same line 321 during half the time, $(\pi)/(N\omega)$. A switch 322, synchronized by the clock 300, allows switching of the two current values $\sin n\theta$ and $\sin (N-n)\theta$ to be carried out, the first to the no. 1 generator referenced 33 and the second to the no. 2 generator referenced 34. These generators 33, 34 allow the various control voltages for the deflection plates 3, 30 and 4, 40 to be obtained from the values $\sin n\theta$ and $\sin (N-n)\theta$, as shown above.

The diameter of the circle on the screen is adjusted by the scale factor generator 35. At its output, this gives an amplification gain control voltage for the generators 33, 34. This control voltage is also adjustable as required by the observer as a function of the sizes of the tube tested and the image required. The gain control voltage is also supplied to the pulse generator 31 for developing the beam pulse generator.

In FIG. 8, the image circle is represented in the digital mode proposed in this variant of the invention. It is therefore composed consecutively of points such as 37 at a fixed distance from the centre of the screen 5 with an angular spacing or angular step $\theta$.

When a fissure forms, an acoustic source is therefore constituted whose position is required to be known. The encoding logic constituted by the detectors 26, 27 operates as already described in the application. The signals S1 allow the clock 300 to be restarted at the values corresponding to the positions at $\pi/3$ either side of the image points of each of the sensors. Thus, when the signal S1A is active, the clock 30 is initialized on the value $n\theta = 0°$ in accordance with the polar axis being at '0' in FIG. 1b. The beam W1 is therefore positioned on the point 0' as in the first embodiment described.

The value $n\theta=0$ therefore corresponds to the first address in the ROM 32. It is present at the output for $\pi/\omega$ seconds, and then a new address for initialization of the second beam is supplied. This address corresponds to $p\theta=120°$ for the point 0'' in FIG. 1b, which allows the second beam to be properly positioned on 0''.

The addresses of the ROM 32 are then incremented by 1 unit at each first half-period in order to travel around the circle in the trigonometrical direction and decreased by 1 unit at each other half-period. These two operations are carried out close to modulo N, and for the four quadrants of the trigonometrical circle.

When one of the signals S2 changes to the active level for the first time, the beam control generator 19 selects one or other of the beams W1 or W2. The two wires 350 and 351 are connected to the outputs of the OR gates 191 and 193.

The scale factor generator 35 includes, as represented in FIG. 9, a RAM memory 353, a temporary memory 356, an adder 354 and the $V_o$ voltage control 355. In normal operation, the function of this generator is to provide the imaging scale reduction factor. In working with the appearance of fissures, it must also obtain incrementation in jumps on the radius of the image point S' of FIG. 8, so that the number of acoustic emissions coming from the same source is accounted for. In the case of FIG. 8, it is noted that the point S' includes three illuminated points 38, 39 and 400. They correspond to three responses of the detector according to the invention. This allows the size of a fissure to be noted as it forms.

FIG. 9 shows a particular embodiment of the scale factor generator 35. Each point of the image circle on the screen 5 has an address which corresponds to a digital position of one or other of the beams W1 or W2, available on the line 320. This line 320 supplies the addresses of each of these points, the RAM 353 thus representing a list of all the points of the circle. Its content is the number of echoes and of sonic pulses picked up by the apparatus according to the invention for each point of the circle. When an address arrives at the generator 35 over the line 320, it is stored for a brief instant in a single address buffer 356. It selects a predetermined location in the RAM. If the function W1.W2, produced by the OR gate 353 is active, the RAM memory 353 is read at its selected address. Its content is sent via D OUT to the input 3540 of a unit incrementer 354.

The result of the addition is transmitted via the output 3542 of the incrementer to DIN of the memory 353 on the one hand, and to the control of the radius generator termed the $V_o$ voltage control circuit 353, on the other. The latter which, when empty, determines the radius r of the image on the screen 5 and the scale factor $(r)/(2R)$, determines the trace for example of as many points outside the image circle of the section, along the radius of the point addressed, as the content of the RAM memory 353 indicates. Thus, in FIG. 8, if address number 1 is attributed to the image point 37, at the address number 2, where three successive echoes 38–400 have been represented, the RAM memory 353 will contain the value 3. This value indicates that, at the instant the section is displayed, the address point 2 has sent three acoustic pulses displayed at 38–400.

The beam control generator 19, which has selected W1 or W2, receives the command to write the last point from the generator 35. In the example of FIG. 8, this generator 19 receives the command to write the point 400 at the end of the calculation carried out by the incrementer 354.

Other embodiments can be proposed which are within the scope of the invention. In particular, it is possible to carry out the operations described with a small microprocessor system built with the ROM 32 and the RAM 33. The form of the circuits described can change with the choice of section. For example, for a metal framework formed of closed triangles, a triangle being the section examined, the apparatus according to the invention must include a generator of graphical triangles on the screen of the dual trace oscilloscope.

Monitoring is carried out with at least three sensors per section. The section is monitored by means of an apparatus which allows only acoustic emissions in the section to be taken into account, by spatial discrimination. Guard sensors are positioned on the structure, either side of the section monitored. The thickness of this can thus be adjusted.

We claim:

1. An acoustic emission locator for locating defects which produce an acoustical wave along the periphery of a fluid carrying enclosure comprising:
   a plurality of at least three acoustic sensors uniformly located along the periphery of the fluid carrying structure;
   means connected to said sensors for shaping the signals received therefrom;
   logic means for receiving shaped signals from said means for shaping for encoding the order of arrival of said sensor's signals including a detector for the first sensor reached by said acoustical wave, and a detector for the second sensor to be reached by said acoustical wave;
   circuit means connected to receive signals from said detectors and generating timing signals representing the time that first and second acoustic sensors receive said acoustic wave;
   display means having a cathode ray tube with two deflection beams for writing on said cathode ray tube face, and first and second identical curve generators connected to first and second deflection control means for controlling positions of respective deflection beams, a pulse rate generator for controlling the deflection rate of said beams, a phase generator means for controlling the angular position of said beams along a line representing the periphery of said fluid carrying enclosure, a scale factor control means for controlling the magnitude of each of said beam's deflections; and
   means for energizing said electron beams to write on said cathode ray tube at a position identified by said timing signals representing the time said first and second acoustic sensors receive said acoustic wave whereby said display means provides a graphic illustration of a defect with respect to known positions of said plurality of acoustic transducers.

2. Locator according to claim 1, wherein the detector of the first sensor comprises three monostable multivibrators with adjustable time constants, each of the inputs receiving the signal received by one of the sensors and each having initialization inputs receiving a blocking signal through a diode, the detector supplying at each detection of an acoustic signal a single signal and its logical complement representative of the first sensor receiving the acoustic signal.

3. Locator according to claim 2, wherein the diode controlling the initialization input of any one of the multivibrators is each connected to the output of one of the other two multivibrators.

4. Locator according to claim 2, wherein the detector of the second sensor to receive an acoustic signal comprises three monostable multivibrators, each of them receiving:
the signal produced by an OR gate from two of the signals received from said sensors;
the signal corresponding to the complementary output of the multivibrator from said first detector relative to the remaining signal;
and the complementary output of said second sensor multivibrator being connected to two AND gates, each producing the sum of one of the two signals with the input to the multivibrator, the outputs of the detector of the second sensor being combinations of signals taken in pairs.

5. Locator according to claim 4, wherein the means for energizing said electron beam comprises:
a first OR gate which forms the product of the signals corresponding to the second sensor to receive said acoustic wave after the first sensor receives said wave in the trigonometrical direction, and connected to a first amplifier which produces an illumination pulse of predetermined duration;
a second OR gate which produces the product of the signals corresponding to the second sensor to receive said acoustic wave after the first sensor received said acoustic wave in the trigonometrical direction and a second amplifier which produces an illumination pulse of predetermined duration.

6. Locator according to one of claim 5, wherein the scale factor generator comprises:
a RAM memory having a capacity at least equal to that of the ROM memory;
an auxiliary memory;
an adder; a counter (355);
a voltage control amplifier with programable gain, whose output is connected to the curve generators.

7. Locator according to claim 6, wherein the auxiliary memory is a register which contains the address of the scanned point and whose output is connected to the ADDRESSES input of the RAM memory.

8. Locator according to claim 6, wherein the RAM memory can be written only if the product function of the beam illumination pulse is at the active level through an OR gate which receives one illumination pulse on one input and a second illumination pulse on its second input and whose output is connected to the read and write terminals of the RAM memory.

9. Locator according to claim 6, wherein the adder receives the contents of a memory cell addressed by the auxiliary memory, and increments it by one unit and in that the output value of the adder is re-written at the same address, and is supplied as control for the amplifier.

10. Locator according to claim 2, wherein the scale factor control means comprises a voltage source which controls the output level of the curve generators.

11. Locator according to claim 10, wherein the voltage source of the scale factor control means is adjusted by a potentiometer indicating the respective dimensions of the structure monitored and of its image on the screen.

12. Locator according to claim 1, wherein identical curve generators are two concentric circle generators, each comprising a concentric circle generator of sinusoidal voltage and a generator of cosinusoidal voltage.

13. Locator according to claim 12, wherein the pulse generator also includes an apparatus for calibrating the speed of propagation of the acoustic waves along the periphery.

14. Locator according to claim 13, wherein the calibration apparatus includes a user adjustable potentiometer which supplies an analog voltage proportional to the speed of propagation of the acoustic waves.

15. Locator according to claim 13, wherein the calibration apparatus comprises:
a switch which excites one of the sensors;
a pulse generator connected to said sensor;
a generator of ramp voltage synchronized with the test pulses;
a detector connected on one of the sensors, said detector blocking the ramp voltage whereby a signal being received identifies the output voltage of the ramp generator corresponding to the propagation time of the acoustic wave between the two sensors, and of the speed of propagation of the acoustic wave.

16. A locator according to claim 1 wherein said phase generator means which selects an initial position for said beams comprises a plurality of voltage sources, each providing an output voltage representing the beam position which corresponds to a sensor position, and switch means for selecting one of said output voltages in accordance with which sensor first receives said acoustic signal; and means for positioning said beam in response to said selected voltage.

17. Locator according to claim 16, wherein the voltage sources comprise biased switching transistors which deliver a predetermined voltage in response to a signal on their bases.

18. Locator according to claim 16, the voltage sources comprise resistances which include divider points with predetermined ratios.

19. An acoustic emission locator for locating defects which produce an acoustical wave along the periphery of a fluid carrying enclosure comprising:
a plurality of at least three acoustic sensors located along the periphery of the fluid carrying enclosure;
means for shaping signals emitted by said sensors;
means for encoding the arrival of signals from said three acoustic snesors including a detector for the first sensor reached and a detector for the second sensor to receive said acoustic wave;
circuit means connected to said means for encoding to generate timing signals representing the time that first and second of said acoustic sensors receive said acoustic wave;
a display means having a cathode ray tube, said display means including sweep circuitry means for positioning a writing electron beam along a path representing the periphery of said enclosure; said sweep circuitry means including:
a pulse generator;
a clock which increments with each pulse received from the pulse generator;
a read only memory in which each address relates to a geometric position of the acoustic waves, containing digital values relating to the position of a point on the display surface of said display means, said memory having an address input connected to said clock;
a switch controlled by the output of said pulse generator having two outputs, and an input connected to receive said memory output;

two identical curve generators which receive through the switch the digital values on said read only memory and which in response thereto supplies suitable control voltages to the sweep circuitry means; and means for energizing said electron beam to write on said display means at a position identified by said timing signals representing the time that said first and second acoustic sensors receive said acoustical wave whereby said display means provides a graphic illustration of a defect with respect to the known positions of said plurality of acoustic transducers.

20. Locator according to claim 19, wherein in that the ROM memory (32) is, at each period of the clock, incremented, and the address read corresponding to the beam rotating in the trigonometrical direction, and when decremented, the address read corresponding to the beam rotating in the opposite direction.

21. An acoustic emission locator for detecting the presence of cracks in a welded conduit structure comprising:
- a plurality of acoustic sensors located around the periphery of the welded conduit;
- logic circuit means connected to receive signals from said sensors, said logic circuit means providing first and second signals, the first of which indicates the first sensor to receive an acoustic signal from a crack in said weld, and the second identifying the second of said sensors to receive said acoustic signal;
- display means including a dual beam cathode ray tube, each of said beams being independently positionable with respect to a screen of said cathode ray tube, said screen having position coordinates for said beams corresponding to positions of said sensors;
- beam positioning means for continuously sweeping said first and second beams across said screen along a path corresponding to the path of said conduit between said sensors, said positioning means having a phase control for positioning said beams in response to said first signal indicating said first sensor to receive an acoustic signal; and
- beam write control means for maintaining said write beams off until said second signal occurs indicating the second of said acoustic sensors has received a signal, whereby one of said write means is enabled to indicate on said screen a position coordinate of said crack.

22. The locator of claim 21 wherein said beam positioning means comprises:
- first and second sweep circuits for rotating said first and second beams in opposite rotational directions along said path; and
- phase control means for positioning said beams on opposite sides of a coordinate representing the sensor first receiving said acoustic signal prior to rotating said beams in opposite directions.

23. The locator according to claim 22 wherein said beam positioning means includes:
- first sine and cosine signal generator, connected to a first pair of deflection plates of said cathode ray tube;
- second sine and cosine signal generator connected to a second pair of deflector plates of said cathode ray tube; and
- a phase control generator connected to phase control signals produced by said sine and cosine signal generators in response to said first signal whereby the starting position of said beams may be time synchronized with a signal received by said acoustic sensors.

24. The locator according to claim 23 further comprising:
- means for controlling the magnitude of said sine and cosine signal generator output signals whereby a scale factor for said displayed image is produced.

25. An acoustic emission locator for locating defects in a conduit comprising:
- a plurality of acoustic sensors located around the periphery of said conduit for sensing acoustic waves emitted through a crack in said conduit;
- logic circuit means connected to receive signals from said acoustic sensors for generating a first and second signal identifying the first and second of said sensors to receive said acoustic waves;
- a cathode ray tube display means having first and second write beams for forming an image of a point along the periphery of said conduit on a display screen, said display means including:
    first and second sweep generators for moving said first and second beams along a predetermined path;
    a read-only memory connected to said sweep generators, said memory including a plurality of position coordinates for said write beams;
    means for sequential reading from said read-only memory said position coordinates, said means reading out a beginning coordinate in response to said first signal; and
    means for enabling one of said write beams in response to said second signal whereby a trace occurs on said display screen identifying the position of said crack.

* * * * *